United States Patent
Dreyfus et al.

(10) Patent No.: US 6,632,639 B1
(45) Date of Patent: Oct. 14, 2003

(54) **MUTANT *E. COLI* STRAINS, AND THEIR USE FOR PRODUCING RECOMBINANT POLYPEPTIDES**

(75) Inventors: Marc Dreyfus, Paris (FR); Pascal Lopez, Saint-Laurent-du-Pont (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 09/762,481

(22) PCT Filed: Jul. 29, 1999

(86) PCT No.: PCT/FR99/01879

§ 371 (c)(1), (2), (4) Date: May 17, 2001

(87) PCT Pub. No.: WO00/08183

PCT Pub. Date: Feb. 17, 2000

(30) Foreign Application Priority Data

Aug. 7, 1998 (FR) .............................................. 98 10197

(51) Int. Cl.[7] .......................... C12P 21/02; C12N 9/22; C12N 15/70
(52) U.S. Cl. .................. 435/69.1; 435/199; 435/252.33
(58) Field of Search ................................ 435/69.1, 194, 435/252, 33

(56) References Cited

FOREIGN PATENT DOCUMENTS

EP 0 178 863 4/1986

OTHER PUBLICATIONS

I. Iost et al., "The stability of *Escherichia coli* lacZ mRNA depends upon the simultaneity of its synthesis and translation", *EMBO Journal*, vol. 13, No. 13, 1995, pp. 3252–3261.

M. Kido et al., "RNase E polypeptides lacking a carboxyl–terminal half supress a mukB mutation in *Escherichia coli*", *Journal of Bacteriology*, vol. 178, No. 13, Jul. 1996, pp. 3917–3925.

I. Iost, "Couplages entres la synthses . . . " Pascal No.: 97–0507561, *Inist, CNRS* (*Centre National De La Recherche Scientifique*), May 1995.

K.J. McDowell et al., "The N–terminal domain of the rne gene–product has Rnase–E activity and is non–overlapping with the Arginine–rich RNA–binding site", *Journal of Molecular Biology*, vol. 255, No. 3, Jan. 26, 1996, pp. 349–355.

P.J. Lopez et al., "The C–terminal half of the Rnase E, which opganizes the *Escherichia coli* degardosome, participates in mRNA degradation but not rRNA processing in vivo", *Molecular Microbiology*, vol. 33, No. 1, Jul. 1999, pp. 188–199.

*Primary Examiner*—Charles L. Patterson, Jr.
(74) *Attorney, Agent, or Firm*—Young & Thompson

(57) ABSTRACT

The invention concerns the use of *Escherichia coli* (*E. coli*) strains whereof the gene coding for the Rnase E comprises a mutation such that the enzyme produced when said mutated gene is expressed no longer has a degrading activity on mRNA, said mutation more significantly not affecting the growth of *E. coli* strains, for implementing a method for producing specific exogenous recombinant polypeptides.

11 Claims, No Drawings

SEQUENCE LISTING

<160> NUMBER OF SEQ ID NOS: 6

<210> SEQ ID NO 1
<211> LENGTH: 3661

-continued

```
<212> TYPE: DNA
<213> ORGANISM: Escherichia coli
<220> FEATURE:
<221> NAME/KEY: CDS
<222> LOCATION: (441)..(3623)

<400> SEQUENCE: 1
```

| | | |
|---|---|---|
| gaaaaaactg tgagtaagcg ggtgataaat ggtaaaagtc atcttgctat aacaaggctt | 60 |
| gcagtggaat aatgaggccg tttccgtgtc catccttgtt aaaacaagaa attttacgga | 120 |
| ataacccatt ttgcccgacc gatcatccac gcagcaatgg cgtaagacgt attgatcttt | 180 |
| caggcagtta gcgggctgcg ggttgcagtc cttaccggta gatggaaata tttctggaga | 240 |
| gtaatacccca gtctgttttct tgtataattg cgctgttttt ccgcatgaaa acgggcaac | 300 |
| cgacactctg cgcctctttg agctgacgat aaccgtgagg ttggcgacgc gactagacac | 360 |
| gaggccatcg gttcacaccc ggaaaggcgt tactttgccc gcagcttagt cgtcaatgta | 420 |

```
agaataatga gtaagttacg atg aaa aga atg tta atc aac gca act cag cag       473
                        Met Lys Arg Met Leu Ile Asn Ala Thr Gln Gln
                          1               5                  10 gaa gag ttg cgc gtt gcc ctt gta gat ggg cag cgt ctg tat gac ctg         521
Glu Glu Leu Arg Val Ala Leu Val Asp Gly Gln Arg Leu Tyr Asp Leu
             15                  20                  25 gat atc gaa agt cca ggg cac gag cag aaa aag gca aac atc tac aaa         569
Asp Ile Glu Ser Pro Gly His Glu Gln Lys Lys Ala Asn Ile Tyr Lys
         30                  35                  40 ggt aaa atc acc cgc att gaa ccg agt ctg gaa gct gct ttt gtt gat         617
Gly Lys Ile Thr Arg Ile Glu Pro Ser Leu Glu Ala Ala Phe Val Asp
     45                  50                  55 tac ggc gct gaa cgt cac ggt ttc ctc cca cta aaa gaa att gcc cgc         665
Tyr Gly Ala Glu Arg His Gly Phe Leu Pro Leu Lys Glu Ile Ala Arg
 60                  65                  70                  75 gaa tat ttc cct gct aac tac agt gct cat ggt cgt ccc aac att aaa         713
Glu Tyr Phe Pro Ala Asn Tyr Ser Ala His Gly Arg Pro Asn Ile Lys
                 80                  85                  90 gat gtg ttg cgt gaa ggt cag gaa gtc att gtt cag atc gat aaa gaa         761
Asp Val Leu Arg Glu Gly Gln Glu Val Ile Val Gln Ile Asp Lys Glu
             95                 100                 105 gag cgc ggc aac aaa ggc gcg gca tta acc acc ttt atc agt ctg gcg         809
Glu Arg Gly Asn Lys Gly Ala Ala Leu Thr Thr Phe Ile Ser Leu Ala
        110                 115                 120 ggt agc tat ctg gtt ctg atg ccg aac aac ccg cgc gcg ggt ggc att         857
Gly Ser Tyr Leu Val Leu Met Pro Asn Asn Pro Arg Ala Gly Gly Ile
    125                 130                 135 tct cgc cgt atc gaa ggc gac gac cgt acc gaa tta aaa gaa gca ctg         905
Ser Arg Arg Ile Glu Gly Asp Asp Arg Thr Glu Leu Lys Glu Ala Leu
140                 145                 150                 155 gca agc ctt gaa ctg ccg gaa ggc atg ggg ctt atc gtg cgc acc gct         953
Ala Ser Leu Glu Leu Pro Glu Gly Met Gly Leu Ile Val Arg Thr Ala
                160                 165                 170 ggc gtc ggc aaa tct gct gag gcg ctg caa tgg gat tta agc ttc cgt        1001
Gly Val Gly Lys Ser Ala Glu Ala Leu Gln Trp Asp Leu Ser Phe Arg
            175                 180                 185 ctg aaa cac tgg gaa gcc atc aaa aaa gcc gct gaa agc cgc ccg gcc        1049
Leu Lys His Trp Glu Ala Ile Lys Lys Ala Ala Glu Ser Arg Pro Ala
        190                 195                 200 ccg ttc ctg att cat cag gag agc aac gta atc gtt cgc gca ttc cgc        1097
Pro Phe Leu Ile His Gln Glu Ser Asn Val Ile Val Arg Ala Phe Arg
    205                 210                 215 gat tac tta cgt cag gac atc ggc gaa atc ctt atc gat aac ccg aaa        1145
```

```
                                                                        -continued Asp Tyr Leu Arg Gln Asp Ile Gly Glu Ile Leu Ile Asp Asn Pro Lys
220                 225                 230                 235 gtg ctc gaa ctg gca cgt cag cat atc gct gca tta ggt cgc ccg gat     1193
Val Leu Glu Leu Ala Arg Gln His Ile Ala Ala Leu Gly Arg Pro Asp
                    240                 245                 250 ttc agc agc aaa atc aaa ctg tac acc ggc gag atc ccg ctg ttc agc     1241
Phe Ser Ser Lys Ile Lys Leu Tyr Thr Gly Glu Ile Pro Leu Phe Ser
                255                 260                 265 cac tac cag atc gag tca cag atc gag tcc gcc ttc cag cgt gaa gtt     1289
His Tyr Gln Ile Glu Ser Gln Ile Glu Ser Ala Phe Gln Arg Glu Val
            270                 275                 280 cgt ctg ccg tct ggt ggt tcc att gtt atc gac agc acc gaa gcg tta     1337
Arg Leu Pro Ser Gly Gly Ser Ile Val Ile Asp Ser Thr Glu Ala Leu
        285                 290                 295 acg gcc atc gac atc aac tcc gca cgc gcg acc cgc ggc ggc gat atc     1385
Thr Ala Ile Asp Ile Asn Ser Ala Arg Ala Thr Arg Gly Gly Asp Ile
300                 305                 310                 315 gaa gaa acc gcg ttt aac act aac ctc gaa gct gcc gat gag att gct     1433
Glu Glu Thr Ala Phe Asn Thr Asn Leu Glu Ala Ala Asp Glu Ile Ala
                320                 325                 330 cgt cag ctg cgc ctg cgt gac ctc ggc ggc ctg att gtt atc gac ttc     1481
Arg Gln Leu Arg Leu Arg Asp Leu Gly Gly Leu Ile Val Ile Asp Phe
                335                 340                 345 atc gac atg acg cca gta cgc cac cag cgt gcg gta gaa aac cgt ctg     1529
Ile Asp Met Thr Pro Val Arg His Gln Arg Ala Val Glu Asn Arg Leu
            350                 355                 360 cgt gaa gcg gtg cgt cag gac cgt gcg cgt att caa atc agc cat att     1577
Arg Glu Ala Val Arg Gln Asp Arg Ala Arg Ile Gln Ile Ser His Ile
        365                 370                 375 tct cgc ttt ggc ctg ctg gaa atg tcc cgt cag cgc ctg agc cca tca     1625
Ser Arg Phe Gly Leu Leu Glu Met Ser Arg Gln Arg Leu Ser Pro Ser
380                 385                 390                 395 ctg ggt gaa tcc agt cat cac gtt tgt ccg cgt tgt tct ggt act ggc     1673
Leu Gly Glu Ser Ser His His Val Cys Pro Arg Cys Ser Gly Thr Gly
                400                 405                 410 acc gtg cgt gac aac gaa tcg ctg tcg ctc tct att ctg cgt ctg atc     1721
Thr Val Arg Asp Asn Glu Ser Leu Ser Leu Ser Ile Leu Arg Leu Ile
                415                 420                 425 gaa gaa gaa gcg ctg aaa gag aac acc cag gaa gtt cac gcc att gtt     1769
Glu Glu Glu Ala Leu Lys Glu Asn Thr Gln Glu Val His Ala Ile Val
            430                 435                 440 cct gtg cca atc gct tct tac ctg ctg aat gaa aaa cgt tct gcg gta     1817
Pro Val Pro Ile Ala Ser Tyr Leu Leu Asn Glu Lys Arg Ser Ala Val
        445                 450                 455 aat gcc att gaa act cgt cag gac ggt gtg cgc tgt gta att gtg cca     1865
Asn Ala Ile Glu Thr Arg Gln Asp Gly Val Arg Cys Val Ile Val Pro
460                 465                 470                 475 aac gat cag atg gaa acc ccg cac tac cac gtg ctg cgc gtg cgt aaa     1913
Asn Asp Gln Met Glu Thr Pro His Tyr His Val Leu Arg Val Arg Lys
                480                 485                 490 ggg gaa gaa acc cca acc tta agc tac atg ctg ccg aag ctg cat gaa     1961
Gly Glu Glu Thr Pro Thr Leu Ser Tyr Met Leu Pro Lys Leu His Glu
                495                 500                 505 gaa gcg atg gcg ctg ccg tct gaa gaa gag ttc gct gaa cgt aag cgt     2009
Glu Ala Met Ala Leu Pro Ser Glu Glu Glu Phe Ala Glu Arg Lys Arg
            510                 515                 520 ccg gaa caa cct gcg ctg gca acc ttt gcc atg ccg gat gtg ccg cct     2057
Pro Glu Gln Pro Ala Leu Ala Thr Phe Ala Met Pro Asp Val Pro Pro
        525                 530                 535
```

```
gcg cca acg cca gct gaa cct gcc gcg cct gtt gta gct cca gca ccg    2105
Ala Pro Thr Pro Ala Glu Pro Ala Ala Pro Val Val Ala Pro Ala Pro
540                 545                 550                 555 aaa gct gca ccg gca aca cca gca gct cct gca caa cct ggg ctg ttg    2153
Lys Ala Ala Pro Ala Thr Pro Ala Ala Pro Ala Gln Pro Gly Leu Leu
            560                 565                 570 agc cgc ttc ttc ggc gca ctg aaa gcg ctg ttc agc ggt ggt gaa gaa    2201
Ser Arg Phe Phe Gly Ala Leu Lys Ala Leu Phe Ser Gly Gly Glu Glu
        575                 580                 585 acc aaa ccg acc gag caa cca gca ccg aaa gca gaa gcg aaa ccg gaa    2249
Thr Lys Pro Thr Glu Gln Pro Ala Pro Lys Ala Glu Ala Lys Pro Glu
    590                 595                 600 cgt caa cag gat cgt cgc aag cct cgt cag aac aac cgc cgt gac cgt    2297
Arg Gln Gln Asp Arg Arg Lys Pro Arg Gln Asn Asn Arg Arg Asp Arg
605                 610                 615 aat gag cgc cgc gac acc cgt agt gaa cgt act gaa ggc agc gat aat    2345
Asn Glu Arg Arg Asp Thr Arg Ser Glu Arg Thr Glu Gly Ser Asp Asn
620                 625                 630                 635 cgc gaa gaa aac cgt cgt aat cgt cgc cag gca cag cag cag act gcc    2393
Arg Glu Glu Asn Arg Arg Asn Arg Arg Gln Ala Gln Gln Gln Thr Ala
            640                 645                 650 gag acg cgt gag agc cgt cag cag gct gag gta acg gaa aaa gcg cgt    2441
Glu Thr Arg Glu Ser Arg Gln Gln Ala Glu Val Thr Glu Lys Ala Arg
        655                 660                 665 acc gcc gac gag cag caa gcg ccg cgt cgt gaa cgt agc cgc cgc cgt    2489
Thr Ala Asp Glu Gln Gln Ala Pro Arg Arg Glu Arg Ser Arg Arg Arg
    670                 675                 680 aat gat gat aaa cgt cag gcg caa caa gaa gcg aag gcg ctg aat gtt    2537
Asn Asp Asp Lys Arg Gln Ala Gln Gln Glu Ala Lys Ala Leu Asn Val
685                 690                 695 gaa gag caa tct gtt cag gaa acc gaa cag gaa gaa cgt gta cgt ccg    2585
Glu Glu Gln Ser Val Gln Glu Thr Glu Gln Glu Glu Arg Val Arg Pro
700                 705                 710                 715 gtt cag ccg cgt cgt aaa cag cgt cag ctc aat cag aaa gtg cgt tac    2633
Val Gln Pro Arg Arg Lys Gln Arg Gln Leu Asn Gln Lys Val Arg Tyr
            720                 725                 730 gag caa agc gta gcc gaa gaa gcg gta gtc gca ccg gtg gtt gaa gaa    2681
Glu Gln Ser Val Ala Glu Glu Ala Val Val Ala Pro Val Val Glu Glu
        735                 740                 745 act gtc gct gcc gaa cca att gtt cag gaa gcg cca gct cca cgc aca    2729
Thr Val Ala Ala Glu Pro Ile Val Gln Glu Ala Pro Ala Pro Arg Thr
    750                 755                 760 gaa ctg gtg aaa gtc ccg ctg cca gtc gta gcg caa act gca cca gaa    2777
Glu Leu Val Lys Val Pro Leu Pro Val Val Ala Gln Thr Ala Pro Glu
765                 770                 775 cag caa gaa gag aac aat gct gat aac cgt gac aac ggt ggc atg ccg    2825
Gln Gln Glu Glu Asn Asn Ala Asp Asn Arg Asp Asn Gly Gly Met Pro
780                 785                 790                 795 cgt cgt tct cgc cgc tcg cct cgt cac ctg cgc gta agt ggt cag cgt    2873
Arg Arg Ser Arg Arg Ser Pro Arg His Leu Arg Val Ser Gly Gln Arg
            800                 805                 810 cgt cgt cgc tat cgt gac gag cgt tat cca acc cag tcg cca atg ccg    2921
Arg Arg Arg Tyr Arg Asp Glu Arg Tyr Pro Thr Gln Ser Pro Met Pro
        815                 820                 825 ttg acc gta gcg tgc gcg tct ccg gaa ctg gcc tct ggc aaa gtc tgg    2969
Leu Thr Val Ala Cys Ala Ser Pro Glu Leu Ala Ser Gly Lys Val Trp
    830                 835                 840 atc cgc tat cca att gta cgt ccg caa gat gta cag gtt gaa gag cag    3017
Ile Arg Tyr Pro Ile Val Arg Pro Gln Asp Val Gln Val Glu Glu Gln
845                 850                 855
```

-continued

```
cgc gaa cag gaa gaa gta cat gtg cag ccg atg gtg act gag gtc cct      3065
Arg Glu Gln Glu Glu Val His Val Gln Pro Met Val Thr Glu Val Pro
860                 865                 870                 875 gtc gcc gcc gct atc gaa ccg gtt gtt agc gcg cca gtt gtt gaa gaa      3113
Val Ala Ala Ala Ile Glu Pro Val Val Ser Ala Pro Val Val Glu Glu
            880                 885                 890 gtg gcc ggt gtc gta gaa gcc ccc gtt cag gtt gcc gaa ccg caa ccg      3161
Val Ala Gly Val Val Glu Ala Pro Val Gln Val Ala Glu Pro Gln Pro
        895                 900                 905 gaa gtg gtt gaa acg acg cat cct gaa gtg atc gct gcc gcg gta act      3209
Glu Val Val Glu Thr Thr His Pro Glu Val Ile Ala Ala Ala Val Thr
    910                 915                 920 gaa cag ccg cag gtg att acc gag tct gat gtt gcc gta gcc cag gaa      3257
Glu Gln Pro Gln Val Ile Thr Glu Ser Asp Val Ala Val Ala Gln Glu
925                 930                 935 gtt gca gaa caa gca gaa ccg gtg gtt gaa ccg cag gaa gag acg gca      3305
Val Ala Glu Gln Ala Glu Pro Val Val Glu Pro Gln Glu Glu Thr Ala
940                 945                 950                 955 gat att gaa gaa gtt gtc gaa act gct gag gtt gta gtt gct gaa cct      3353
Asp Ile Glu Glu Val Val Glu Thr Ala Glu Val Val Val Ala Glu Pro
            960                 965                 970 gaa gtt gtt gct caa cct gcc gcg cca gta gtc gct gaa gtc gca gca      3401
Glu Val Val Ala Gln Pro Ala Ala Pro Val Val Ala Glu Val Ala Ala
        975                 980                 985 gaa gtt gaa acg gta gct gcg gtc gaa cct gag gtc acc gtt gag cat      3449
Glu Val Glu Thr Val Ala Ala Val Glu Pro Glu Val Thr Val Glu His
    990                 995                 1000 aac cac gct acc gcg cca atg acg cgc gct cca gca ccg gaa tat gtt      3497
Asn His Ala Thr Ala Pro Met Thr Arg Ala Pro Ala Pro Glu Tyr Val
1005                1010                1015 ccg gag gca ccg cgt cac agt gac tgg cag cgc cct act ttt gcc ttc      3545
Pro Glu Ala Pro Arg His Ser Asp Trp Gln Arg Pro Thr Phe Ala Phe
1020                1025                1030                1035 gaa ggt aaa ggt gcc gca ggt ggt cat acg gca aca cat cat gcc tct      3593
Glu Gly Lys Gly Ala Ala Gly Gly His Thr Ala Thr His His Ala Ser
            1040                1045                1050 gcc gct cct gcg cgt ccg caa cct gtt gag taataattag ctcaaagtaa        3643
Ala Ala Pro Ala Arg Pro Gln Pro Val Glu
        1055                1060 tcaagccctg gtaactgc                                                  3661

<210> SEQ ID NO 2
<211> LENGTH: 1061
<212> TYPE: PRT
<213> ORGANISM: Escherichia coli

<400> SEQUENCE: 2

Met Lys Arg Met Leu Ile Asn Ala Thr Gln Gln Glu Glu Leu Arg Val
1               5                   10                  15

Ala Leu Val Asp Gly Gln Arg Leu Tyr Asp Leu Asp Ile Glu Ser Pro
            20                  25                  30

Gly His Glu Gln Lys Lys Ala Asn Ile Tyr Lys Gly Lys Ile Thr Arg
        35                  40                  45

Ile Glu Pro Ser Leu Glu Ala Ala Phe Val Asp Tyr Gly Ala Glu Arg
    50                  55                  60

His Gly Phe Leu Pro Leu Lys Glu Ile Ala Arg Glu Tyr Phe Pro Ala
65                  70                  75                  80

Asn Tyr Ser Ala His Gly Arg Pro Asn Ile Lys Asp Val Leu Arg Glu
```

-continued

```
                85                  90                  95
Gly Gln Glu Val Ile Val Gln Ile Asp Lys Glu Arg Gly Asn Lys
                100                 105                 110
Gly Ala Ala Leu Thr Thr Phe Ile Ser Leu Ala Gly Ser Tyr Leu Val
                115                 120                 125
Leu Met Pro Asn Asn Pro Arg Ala Gly Gly Ile Ser Arg Arg Ile Glu
    130                 135                 140
Gly Asp Asp Arg Thr Glu Leu Lys Glu Ala Leu Ala Ser Leu Glu Leu
145                 150                 155                 160
Pro Glu Gly Met Gly Leu Ile Val Arg Thr Ala Gly Val Gly Lys Ser
                165                 170                 175
Ala Glu Ala Leu Gln Trp Asp Leu Ser Phe Arg Leu Lys His Trp Glu
                180                 185                 190
Ala Ile Lys Lys Ala Ala Glu Ser Arg Pro Ala Pro Phe Leu Ile His
            195                 200                 205
Gln Glu Ser Asn Val Ile Val Arg Ala Phe Arg Asp Tyr Leu Arg Gln
    210                 215                 220
Asp Ile Gly Glu Ile Leu Ile Asp Asn Pro Lys Val Leu Glu Leu Ala
225                 230                 235                 240
Arg Gln His Ile Ala Ala Leu Gly Arg Pro Asp Phe Ser Ser Lys Ile
                245                 250                 255
Lys Leu Tyr Thr Gly Glu Ile Pro Leu Phe Ser His Tyr Gln Ile Glu
                260                 265                 270
Ser Gln Ile Glu Ser Ala Phe Gln Arg Glu Val Arg Leu Pro Ser Gly
            275                 280                 285
Gly Ser Ile Val Ile Asp Ser Thr Glu Ala Leu Thr Ala Ile Asp Ile
    290                 295                 300
Asn Ser Ala Arg Ala Thr Arg Gly Gly Asp Ile Glu Glu Thr Ala Phe
305                 310                 315                 320
Asn Thr Asn Leu Glu Ala Ala Asp Glu Ile Ala Arg Gln Leu Arg Leu
                325                 330                 335
Arg Asp Leu Gly Gly Leu Ile Val Ile Asp Phe Ile Asp Met Thr Pro
            340                 345                 350
Val Arg His Gln Arg Ala Val Glu Asn Arg Leu Arg Glu Ala Val Arg
    355                 360                 365
Gln Asp Arg Ala Arg Ile Gln Ile Ser His Ile Ser Arg Phe Gly Leu
    370                 375                 380
Leu Glu Met Ser Arg Gln Arg Leu Ser Pro Ser Leu Gly Glu Ser Ser
385                 390                 395                 400
His His Val Cys Pro Arg Cys Ser Gly Thr Gly Thr Val Arg Asp Asn
                405                 410                 415
Glu Ser Leu Ser Leu Ser Ile Leu Arg Leu Ile Glu Glu Ala Leu
            420                 425                 430
Lys Glu Asn Thr Gln Glu Val His Ala Ile Val Pro Val Pro Ile Ala
            435                 440                 445
Ser Tyr Leu Leu Asn Glu Lys Arg Ser Ala Val Asn Ala Ile Glu Thr
    450                 455                 460
Arg Gln Asp Gly Val Arg Cys Val Ile Val Pro Asn Asp Gln Met Glu
465                 470                 475                 480
Thr Pro His Tyr His Val Leu Arg Val Arg Lys Gly Glu Glu Thr Pro
                485                 490                 495
Thr Leu Ser Tyr Met Leu Pro Lys Leu His Glu Glu Ala Met Ala Leu
            500                 505                 510
```

-continued

Pro Ser Glu Glu Phe Ala Glu Arg Lys Arg Pro Glu Gln Pro Ala
        515                 520                 525

Leu Ala Thr Phe Ala Met Pro Asp Val Pro Ala Pro Thr Pro Ala
        530                 535                 540

Glu Pro Ala Ala Pro Val Val Ala Pro Ala Pro Lys Ala Ala Pro Ala
545                 550                 555                 560

Thr Pro Ala Ala Pro Ala Gln Pro Gly Leu Leu Ser Arg Phe Phe Gly
                565                 570                 575

Ala Leu Lys Ala Leu Phe Ser Gly Gly Glu Thr Lys Pro Thr Glu
        580                 585                 590

Gln Pro Ala Pro Lys Ala Glu Ala Lys Pro Glu Arg Gln Gln Asp Arg
        595                 600                 605

Arg Lys Pro Arg Gln Asn Asn Arg Arg Asp Arg Asn Glu Arg Arg Asp
610                 615                 620

Thr Arg Ser Glu Arg Thr Glu Gly Ser Asp Asn Arg Glu Glu Asn Arg
625                 630                 635                 640

Arg Asn Arg Arg Gln Ala Gln Gln Thr Ala Glu Thr Arg Glu Ser
                645                 650                 655

Arg Gln Gln Ala Glu Val Thr Glu Lys Ala Arg Thr Ala Asp Glu Gln
        660                 665                 670

Gln Ala Pro Arg Arg Glu Arg Ser Arg Arg Asn Asp Asp Lys Arg
        675                 680                 685

Gln Ala Gln Gln Glu Ala Lys Ala Leu Asn Val Glu Glu Gln Ser Val
        690                 695                 700

Gln Glu Thr Glu Gln Glu Glu Arg Val Arg Pro Val Gln Pro Arg Arg
705                 710                 715                 720

Lys Gln Arg Gln Leu Asn Gln Lys Val Arg Tyr Glu Gln Ser Val Ala
                725                 730                 735

Glu Glu Ala Val Val Ala Pro Val Val Glu Glu Thr Val Ala Ala Glu
                740                 745                 750

Pro Ile Val Gln Glu Ala Pro Ala Pro Arg Thr Glu Leu Val Lys Val
        755                 760                 765

Pro Leu Pro Val Val Ala Gln Thr Ala Pro Glu Gln Gln Glu Glu Asn
770                 775                 780

Asn Ala Asp Asn Arg Asp Asn Gly Gly Met Pro Arg Arg Ser Arg Arg
785                 790                 795                 800

Ser Pro Arg His Leu Arg Val Ser Gly Gln Arg Arg Arg Tyr Arg
                805                 810                 815

Asp Glu Arg Tyr Pro Thr Gln Ser Pro Met Pro Leu Thr Val Ala Cys
                820                 825                 830

Ala Ser Pro Glu Leu Ala Ser Gly Lys Val Trp Ile Arg Tyr Pro Ile
        835                 840                 845

Val Arg Pro Gln Asp Val Gln Val Glu Glu Gln Arg Glu Gln Glu Glu
        850                 855                 860

Val His Val Gln Pro Met Val Thr Glu Val Pro Val Ala Ala Ile
865                 870                 875                 880

Glu Pro Val Val Ser Ala Pro Val Val Glu Glu Val Ala Gly Val Val
                885                 890                 895

Glu Ala Pro Val Gln Val Ala Glu Pro Gln Pro Glu Val Val Glu Thr
        900                 905                 910

Thr His Pro Glu Val Ile Ala Ala Ala Val Thr Glu Gln Pro Gln Val
        915                 920                 925

Ile Thr Glu Ser Asp Val Ala Val Ala Gln Glu Val Ala Gln Ala
        930                 935                 940

Glu Pro Val Val Glu Pro Gln Glu Thr Ala Asp Ile Glu Val
945                 950                 955                 960

Val Glu Thr Ala Glu Val Val Ala Glu Pro Glu Val Val Ala Gln
                965                 970                 975

Pro Ala Ala Pro Val Val Ala Glu Val Ala Ala Glu Val Glu Thr Val
            980                 985                 990

Ala Ala Val Glu Pro Glu Val Thr Val Glu His Asn His Ala Thr Ala
        995                 1000                1005

Pro Met Thr Arg Ala Pro Ala Pro Glu Tyr Val Pro Glu Ala Pro Arg
    1010                1015                1020

His Ser Asp Trp Gln Arg Pro Thr Phe Ala Phe Glu Gly Lys Gly Ala
1025                1030                1035                1040

Ala Gly Gly His Thr Ala Thr His His Ala Ser Ala Ala Pro Ala Arg
                1045                1050                1055

Pro Gln Pro Val Glu
        1060

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggctgcagt ttccgtgtcc atccttg                                          27

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggagatctt gattactttg agctaa                                           26

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctgcagatag cccgcctaat gagcgggctt ttttttctgc ag                         42

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcggtggtta agaaaccaaa c                                                21

MUTANT E. COLI STRAINS, AND THEIR USE FOR PRODUCING RECOMBINANT POLYPEPTIDES

The invention concerns certain mutant E. coli strains, and their use for performing processes for producing recombinant polypeptides.

Genomic study of higher organisms, micro-organisms, and viruses almost invariably requires, in addition to the cloning of their genes, large-scale production of their products (proteins), so as for example to obtain antibodies or to perform biochemical or crystallographic studies.

From the applications viewpoint, the utilization in the medical field of numerous human peptides and proteins also requires expression of corresponding genes in heterologous organisms.

Although expression systems have been established in various eukaryotic hosts (especially in yeasts, insects and primate cells), the most widely used host for these expression strategies remains the bacteria Escherichia coli (E. coli). The list of proteins of biotechnological or pharmacological interest that are produced in E. coli is extensive; classic examples include human insulin and human growth hormone.

The most well-known expression system in, prokaryotes was developed in the USA by the Studier and Richardson groups, during the 1980's (Tabor and Richardson, 1985; Studier and Moffat, 1986). It is based on exploiting the properties of T7 RNA polymerase (namely RNA polymerase encoded by the T7 bacteriophage). That enzyme, which can be expressed in E. coli cells without toxicity, recognizes a very specific promoter. Any gene of interest (target gene) may be transcribed very efficiently, upon placing it downstream of this promoter and introducing it into an E. coli cell expressing T7 polymerase.

Nevertheless, in terms of expression, the results remain uncertain. Some target genes may be duly overexpressed, whereas others are expressed only moderately or not at all.

Previous work by the inventors revealed that one of the principal causes of these setbacks resides in the specific instability of the m-RNA synthesized by T7 RNA polymerase, which causes a decrease in the number of polypeptides synthesized by messaging (Lopez et al., 1994; Iost and Dreyfus, 1994, 1995). This instability is the consequence of the high speed of elongation of T7 RNA polymerase (Makarova et al., 1995). Specifically, the elongation speed of T7 polymerase, in contrast to that of bacterial RNA polymerase, is much greater than the translation speed of m-RNA by ribosomes. Nascent m-RNA is therefore exposed over most of its length, and is therefore readily attacked by nucleases, and in E. coli especially by the E-type ribonuclease (or RNase E), whose amino acid sequence is described by Casaregola et al. (Casaregola et al., 1992, 1994).

RNase E is an essential enzyme of E. coli; it is involved both in the degradation of m-RNA as well as in the maturation of ribosomal RNA (r-RNA). Mutations in the catalytic region (that is, in the N-terminal portion of RNase E) affect these two functions at the same time, and slow down or even arrest the growth of E. coli (Cohen and McDowall, 1997).

On the other hand, deletions in the C-terminal portion of RNase E do not affect the viability of E. coli. Specifically, by researching revertants of mutations in a protein (MukB) necessary for the segregation of chromosomes after replication, Kido et al. obtained various viable mutations in the rne gene, coding RNase E in E. coli, which cause synthesis of an RNase E that is truncated in its C-terminal portion (Kido et al., 1996). These authors concluded from these experiments that the C-terminal portion of RNase E is not essential for viability of E coli. They moreover formed the hypothesis that suppression of the mukB mutations by truncating of the RNase E, reflects the fact that truncated RNase E is less effective than the wild-type enzyme for degrading mukB m-RNA. Thus stabilized, a stronger synthesis of the mutant MukB protein could be achieved, thereby correcting the phenotype associated with the mutation. However, this stabilization of the mukB messenger was not demonstrated, and other authors proposed an entirely different interpretation to explain the suppressive effect of the truncating of RNase E on mukB mutations (Cohen and McDowall, 1997). These authors postulate in particular a direct interaction between RNase E and MukB. The basis for that idea is the fact that RNase E has a very substantial similarity with eukaryotic myosin (Casaregola et al., 1992: McDowall et al., 1993), which suggests that aside from its own RNase activity, it could, like MukB, play a structural role.

The present invention arises from the demonstration by the inventors of the fact that the truncating of RNase E causes an overall stabilization of cellular m-RNA, considered as a whole, as well as of the majority of individual m-RNAs that were examined, without significantly impeding the maturation of the r-RNAs (Lopez et al., 1999).

In that regard, the effect of the deletion is very different from that of a mutation in the N-terminal region, such as the ams mutation (Ono and Kuwano, 1979), renamed rne1 (Babitzke and Kushner, 1991), which confers thermosensitive activity to RNase E. For example, at 37° C., this latter mutation causes a moderate increase in the lifespan of the m-RNAs (1.5 times each on average; the lifespan of the m-RNAs is here defined as the time during which they serve as a matrix for protein synthesis (Mudd et al., 1990a)), but it also causes a significant slowdown in maturation of the r-RNAs (estimated by the "Northern" method; see Lopez et al., 1994) and it retards the growth by a factor of 2. On the contrary, deletion of the C-terminal portion of RNase E, especially of amino acids 586 to 1061 of this latter, causes a more significant stabilization of the m-RNA (two times on average), without causing a slowdown in the maturation of the r-RNA and without retarding growth. Thus, in hindsight, it is likely that the lack of growth that was observed with N-terminal mutations of RNase E, is due solely to the inability of the cells to mature r-RNA.

In summary, deletions in the C-terminal portion of RNase E have no effect on the activity of the catalytic domain, judging from the rapid maturation of the r-RNA. That rapid maturation explains why the cells containing such a deletion are viable. On the other hand, the deletion stabilizes the m-RNA as a whole, perhaps because it inhibits the association of the RNase E with other enzymes within a multiprotein structure, the so-called "degradosome", which might be necessary for degradation of the m-RNA (Carpousis et al., 1994; Miczack et al, 1996; Py et al., 1996; Kido et al., 1996; Cohen and McDowall, 1997). The important point from the perspective of the invention is that, by virtue of these deletions, it is possible to obtain E. coli strains having enhanced m-RNA stability, while preserving normal growth.

The inventors have also shown that the stabilization of m-RNA due to the deletion of the C-terminal portion of RNase E, is not uniform, but rather is more pronounced for less stable m-RNA. As is known, this is often the case for the m-RNA of "target" genes in expression systems. The contribution of this m-RNA to the overall protein synthesis is therefore enhanced by the presence of the deletion. E. coli strains comprising such a deletion therefore express recombinant exogenous polypeptides with sharply higher yields (in particular about 3 to 25 times higher) with respect to the expression yields of those recombinant polypeptides by *E. Coli* strains not comprising that mutation, especially when the expression of the said recombinant polypeptides is placed under the control of T7 RNA polymerase.

The present invention therefore has as an object to provide novel processes for producing recombinant proteins or polypeptides from *E. coli*, especially those of pharmaceutical or biological interest, at production yields substantially greater than those of the processes described up to now.

The present invention also has as an object to provide novel *E. coli* strains for practicing the above-mentioned processes, as well as methods for preparing such strains.

The present invention has as an object the use of *E. coli* strains whose gene encoding RNase E comprises a mutation such that the. enzyme produced upon expression of this mutated gene no longer possesses m-RNA-degrading activity, this mutation not significantly affecting the growth of the said *E. coli* strains, for practicing a process for producing predetermined exogenous recombinant polypeptides (or proteins).

The present invention more particularly concerns the use of *E. coli* strains whose gene coding RNase E comprises a mutation such that the enzyme produced upon expression of this mutated gene preserves the maturation activity of the r-RNA of the RNase E, but no longer possesses the degradation activity of the m-RNA, for practicing a process for producing predetermined exogenous recombinant polypeptides (or proteins).

The invention more particularly has as an object the above-mentioned utilization of *E. coli* strains as defined above, characterized in that the mutation consists in the substitution or deletion of one or several nucleotides in a region of the gene coding for the C-terminal portion of RNase E.

The invention yet more particularly concerns the above-mentioned utilization of *E. coli* strains as defined above, characterized in that the mutation corresponds to the substitution or to the deletion of one or several nucleotides of the region delimited by the nucleotide situated at position 1935 and the nucleotide situated at position 3623 of the DNA coding RNase E, represented by SEQ ID NO: 1.

Advantageously, the above-mentioned mutation causes modification or deletion of at least one amino acid from the C-terminal portion of RNase E.

To that end, the invention has as an object the above-mentioned utilization of *E. coli* strains as defined above, characterized in that the mutation causes the deletion of at least one, and up to all, of the last 563 amino acids of the sequence of RNase E represented by SEQ ID NO:2.

The invention more particularly has as an object the above-mentioned utilization of *E. coli* strains as defined above, characterized in that the mutation corresponds to the substitution of the guanine G in position 2196 of SEQ ID NO: 1 by a thymidine T, so as to create a stop codon TAA situated at positions 2196 to 2198 of SEQ ID NO:.

Advantageously, the above-mentioned mutant *E. coli* strains, used in the context of the invention, contain an exogenous inducible expression system, under the control of which is placed the expression of predetermined recombinant polypeptides, especially the inducible expression system using RNA polymerase of the T7 bacteriophage.

The invention also concerns *E. coli* strains that are transformed such that they contain an exogenous inducible expression system, and whose gene coding RNase E comprises a mutation such that the enzyme produced upon expression of this mutated gene no longer possesses degradation activity for m-RNA, this mutation not significantly affecting growth of the said *E. coli* strains.

The invention also has for an object *E. coli* strains such as described above, transformed such that they contain an exogenous inducible expression system, notably chosen from those described above, and whose gene coding RNase E comprises a mutation such that the enzyme produced upon expression of this mutated gene preserves the maturation activity for the r-RNA of the RNase E, but no longer possesses the activity of this latter for degradation of m-RNA.

The invention more particularly has as an object *E. coli* strains as described above, characterized in that the inducible expression system uses RNA polymerase coded by the T7 bacteriophage.

The invention also concerns *E. coli* strains as described above, characterized in that the mutation consists in the substitution or deletion of one or several nucleotides from the region of the gene coding for the C-terminal portion of RNase E.

The invention yet more particularly concerns *E. coli* strains as defined above, characterized in that the mutation corresponds to the substitution or deletion of one or several nucleotides from the region delimited by the nucleotide situated at position 1935 and the nucleotide situated at position 3623 of the DNA sequence coding RNase E, represented by SEQ ID NO: 1.

The invention more particularly has for an object mutant *E. coli* strains as defined above, characterized in that the above-mentioned mutation causes modification or deletion of at least one amino acid of the C-terminal portion of the RNase E expressed by the said strains.

To that end, the invention has as an object *E. coli* strains as defined above, characterized in that the mutation causes deletion of at least one, up to all, of the last 563 amino acids of the sequence of RNase E represented by SEQ ID NO: 2.

The invention more particularly has as an object *E. coli* strains as defined above, characterized in that the mutation corresponds to the substitution of guanine G at position 2196 of SEQ ID NO: 1, by thymidine T, so as to create a stop codon TAA situated at positions 2196 to 2198 of SEQ ID NO: 1.

The invention also has as an object *E. coli* strains as defined above, characterized in that the inducible expression system controls the transcription of a DNA sequence coding one or several predetermined recombinant polypeptides.

The invention also concerns any process for producing predetermined recombinant polypeptides, characterized in that it comprises:

a step of transforming *E. coli* strains whose gene coding RNase E comprises a mutation such that the enzyme produced upon expression of this mutated gene no longer possesses degradation activity for m-RNA, this mutation not significantly affecting the growth of the said *E. coli* strains, with a vector, especially a plasmid, containing the nucleotide sequence coding one or several recombinant polypeptides, culturing of the transformed *E. coli* strains obtained during the preceding step, for a time sufficient to allow expression of the recombinant polypeptides in the *E. coli* cells, and recovery of the recombinant polypeptide or polypeptides produced during the preceding step, if desired after purification of these latter, especially by chromatography, electrophoresis, or selective precipitation.

The invention more particularly has as an object any process for producing predetermined recombinant polypeptides, as defined above, characterized in that it comprises:

a step of transforming *E. coli* strains as described above, with a vector, especially a plasmid, containing the nucleotide sequence coding one or several recombinant polypeptides, so as to obtain the above-mentioned *E. coli* strains, in which transcription of the said nucleotide sequence coding one or several recombinant polypeptides is placed under the control of an inducible expression system, culturing the transformed *E. coli* strains obtained during the preceding step, and inducing the said expression system, for a time sufficient to permit expression of the recombinant polypeptide or polypeptides in *E. coli* cells, the inducing of the said expression system especially being effected by causing synthesis of T7 RNA polymerase when the said expression system calls for that polymerase; this synthesis may notably be provoked by adding IPTG to the culture medium, or by raising the temperature, following which the gene coding for this RNA polymerase is placed under the control of a promoter regulated by the lac repressor (Studier and Moffat, 1986), or under the control of a thermo-inducible promoter (Tabor and Richardson, 1985), and recovering the recombinant polypeptide or polypeptides produced during the preceding step.

A general process for obtaining mutant *E. coli* strains as described above, and capable of being used in the context of the present invention, comprises the following steps:

preparation of a plasmid containing an rne gene comprising a mutation as described above, and in which the promoter of the said rne gene is suppressed, introduction of the plasmid obtained in the preceding step, into an *E. coli* strain comprising an inducible expression system, as well as a chromosomal mutation in the rne gene conferring a particular property to the said *E. coli*, such that the so-called rne1 mutation (Ono; and Kuwano, 1979) rendering the growth of the host thermosensitive, and permitting selecting acquisition of the desired mutation of the rne gene on the *E. coli* chromosome, culturing the thus-transformed *E. coli* strains, and selecting *E. coli* strains having the particular property mentioned above, namely the clones resulting from the homologous recombination which permits replacing the said chromosomal mutation by the homologous sequence corresponding to the mutated rne gene of the said plasmid, especially selection of thermoresistant clones in the case where the chromosome mutation is the said rne1 mutation, elimination of the plasmid from the selected clones, and identification from among these clones of those comprising the above-mentioned mutated rne gene, especially by analyzing by electrophoresis the length of the truncated RNase E polypeptide, coded by the above-mentioned mutated rne gene, produced by the mutant *E. coli* cells.

The invention will be illustrated to advantage with the aid of the following detailed description of the preparation of a mutant *E. coli* strain according to the invention, and of its use for producing predetermined polypeptides.

1) Construction of a mutant rne gene containing a STOP codon at the 586th codon

This particular position was chosen, as the truncation thus created in the RNase E is formally equivalent to that which results from the spontaneous smbB131 mutation (here renamed rne131) obtained by Kido et al. (1996). This latter is a deletion of 2 nucleotides at the 586th codon, causing a reading frame shift followed by a stop, after a supplementary translation of 32 codons without relation to the normal sequence of RNase E.

To construct such a gene, the G2196 nucleotides of the sequence is substituted by T, creating a TAA codon (stop) at nucleotide 2196–2198 of SEQ ID NO: 1 (this mutation will by convention be designated herein "G2196T").

To create the desired substitution, the wild-type rne gene is first subcloned in the pEMBL8$^+$ "phagemid" (Dente et al., 1983). To that end, the entire transcribed sequence of the rne gene is amplified from the *E. coli* genome, with the aid of the following primers:

SEQ ID NO: 3: 5' GGGCTGCAGTTTCCGTGTCCATC-CTTG 3' (the sequence in bold corresponds to the nucleotides (nt) 81–98 of SEQ ID NO: 1; the sequence in italics is the recognition sequence of the PstI enzyme), and SEQ ID NO: 4: 5' GGGAGATCTTGAT-TACTTTGAGCTAA 3' (the sequence in bold is complementary to nt 3630 to 3647 of SEQ ID NO: 1; the sequence in italics is recognized by the BglII enzyme).

The amplified fragment is then digested by BglII and PstI enzymes (these enzymes have no cleavage sites interiorly of the rne sequence), and inserted between the BamHI and PstI sites of pEMBL8$^+$ (bearing in mind that the BamHI and BglII sites may be ligated to one another). It will be noted that the rne sequence thus cloned is devoid of its promoter.

Any parasitic transcription issuing from the vector is eliminated by next introducing into the PstI sites of the obtained sequence, and in the same direction as the rne gene, the following synthetic fragment:

SEQ ID NO: 5:
CTGCAGATAGCCCGCCTAAT-GAGCGGGCTTTTTTTTCTGCAG (the sequence in bold corresponds to a very efficient transcription terminator, of the tryptophan operon (Christie et al., 1981), and the extremities in italics correspond to the sequence recognized by PstI). These precautions guarantee that the rne sequence carried by the plasma may not be transcribed from plasmid promoters, and thus that the RNase E may not be synthesized from the plasmid. The significance of this point will appear later. In the following description, the plasmid thus obtained is named pRNE.

The desired substitution (G→T) is then introduced; into the pRNE plasmid by using the conventional technique of directed mutagenesis described by Kunkel (Kunkel et al., 1987). For that, the pRNE plasmid is introduced into the RZ1032 strain (Hfr KL16PO/45 (lysA61–62 dut1 ung1 thi1 relA1 supE44 zbd-279::Tn10). The dut1 and ung1 mutations present in this strain cause incorporation of deoxyuridine (dU) in place of thymidin (T) in the DNA. The cells are next overinfected by the K07 "helper" M13 phage (Pharmacia), which causes accumulation in the medium of "phages" comprising the sequence of pRNE in the form of a simple strand, with dU in place of T. After deproteinization, this single strand matrix is hybridized with the following synthetic oligonucleotide:

SEQ ID NO: 6: GCGGTGGTTAAGAAACCAAAC corresponding to the positions 2188 to 2208 of SEQ ID NO:1 (the "T" that is desired to be incorporated in place of G is indicated in bold), then the hybrid is converted to double strand DNA by incubation with Klenow polymerase, T4 ligase, ATP and DNTP (Kunkel et al., 1987). The double strand hybrid is then introduced in XL1, an *E. coli* strain conventionally used for cloning (Stratagene). This strain is native for the dut and ung genes, and consequently the initial strand comprising dU in place of T will be degraded. The vast majority of the resulting XL1 colonies thus, comprise the desired mutation in the pRNE plasmid.

By choosing four candidates, it is assured that the desired mutation is clearly present, and that the plasmid does not comprise any others. In that regard, appropriate oligonucleotide primers are used to determine the sequence of the AflII-NruI region (nt 1931–2345 of SEQ ID NO: 1), and only those candidates comprising in this region the single desired mutation are selected, to the exclusion of any other modification. The AflII-NruI fragment issuing from such a candidate is then isolated and the AflII-NruI fragment of the initial (non-mutagenizised) pRNE plasma is substituted therein. There is thus obtained a plasmid comprising the desired mutation; this plasmid is designated hereinafter as pRNE-STOP.

2) Introduction of the mutation creating a stop at codon 586 of RNase E, on the BL21(DE3) chromosome, a strain expressing the RNA polymerase of the T7 bacteriophage General principle. The desired mutation (G2196T) produces no phenotype change relative to the wild-type gene. To introduce it onto the chromosome, it is therefore necessary to proceed in two steps: first, a false-direction mutation is introduced into RNase E at codon 66 (the mutation designated ams, or rne1; Ono and Kuwano, 1979). This mutation corresponds to the G636A transition, according to the numbering of SEQ ID NO: 1 (McDowall et al., 1993). It decreases the thermal stability of the RNase E, impeding high temperature growth.

Next, the pRNE-stop plasmid is introduced into the resulting strain, and the cells that are able to grow anew at high temperature are selected. It will be recalled that the rne-stop gene carried by the plasma, being non-transcribed, does not lead to the synthesis of a functional RNase E. In any event, by virtue of a homologous double recombination, the plasmid can carry to the chromosomal rne gene the wild-type sequence at position 636 (A636G mutation), reestablishing at the same time the high temperature growth. The homologous region between the plasmid and the chromosomal rne region extending over about 1500 nt downstream of the G2196T mutation carried by the plasma, this latter mutation has a strong likelihood of being transferred onto the chromosome at the same time as a A636G. The plasmid is then eliminated; the result is a strain comprising the sole mutation G2196T in the chromosomal gene of RNase E.

Preparation of an rne1 (ams) derivative of the BL21(DE3) strain. BL21(DE3) is the typical host for bacterial expression systems based on transcription of heterologous genes by T7 polymerase (Studier & Moffat, 1986). Techniques permitting introduction of the rne mutation in, any desired genetic context have been described, especially for BL21 (DE3) and its derivatives (Mudd et al., 1990b; Iost & Dreyfus, 1995). Briefly, one starts from a bacterial strain (CH1828), comprising the ams/rne1 mutation as well as a tetracycline resistance gene inserted in a chromosomal locus (zce-726) situated a short distance from the rne gene. Using the conventional technique known as P1 bacteriophage transduction (Silhavy et al., 1984), a long region of the CH1828 chromosome of several tens of thousands of nucleotides and surrounding the zce-726 locus, is transferred into BL21(DE3), by selecting acquisition of resistance to tetracycline (Tet$^R$). A high proportion (about 50%) of these Tet$^R$ clones also display thermosensitive growth, which indicates that they have also received the rne1 allele. The resulting strain is named BL21(DE3)rne1.

Introduction of the G2196T mutation onto the BL21 (DE3) chromosome. BL21(DE3)rne1 is transformed with the pRNE-stop plasmid (and, as a control, with the initial plasmid pEMBL8$^+$), then, after growth in complete liquid medium (LB medium; (Miller, 1972)) at 30° C., about $10^5$ bacteria are spread out on Petri dishes containing the same medium in agarose, and then incubated at 42° C. For the control bacteria, no growth was observed after 24 hours (the ams/rne1 mutation does not spontaneously reverse). In contrast, the bacteria transformed with pRNE-stop show a large number of thermoresistant clones, arising from reversion of the chromosomal rne1 mutation by virtue of the wild-type sequence carried by the plasmid. A dozen of these thermoresistant clones are then chosen, and the plasmid is eliminated from these candidates by cultivating without ampicillin for about 20 generations in LB liquid medium (42° C.). Ampicillin is necessary for maintaining plasmids derived from pEMBL8$^+$; in its absence, the plasmid segregates quite readily (Dreyfus, 1988). After re-isolation on LB/agarose medium of the candidates thus treated, loss of the plasmid was verified by testing that the individual colonies could no longer grow in the presence of ampicillin.

It remains to identify those of the thermoresistant revertants—the majority—which, at the same time as the wild-type sequence at position 636, have also acquired the G2196T mutation. This proceeds in two steps. First, the candidates are re-isolated on agarose minimum medium (we use M63B1 medium with glycerol as a carbon source; (Miller, 1972)); by way of control, the BL21(DE3) initial strain and the BL21(DE3) rne1 thermosensitive mutant are also spread out on the same dishes. These are then incubated at 43° C. The G2196T mutation causes a slight slowdown of growth in these extreme conditions; the studied recombinants therefore lead to smaller colonies than the wild-type BL21(DE3) cells, which permits an initial screening for the study of these recombinants. The final test resorts to direct determination of the size of the RNase E polypeptide, using the "Western" immunological technique (Sambrook et al., 1989). Briefly, the various candidates (as well as the two controls mentioned above) are grown in LB liquid medium. When the optical density of the cultures at 600 nm reaches 0.5, the cells are harvested. They are then re-suspended in a phosphate buffer and lysed by sonication. After elimination of debris, the proteins in the cellular extract are determined (Bradford, 1976), and then 20 $\mu$g of the protein mixture is subjected to electrophoresis according to the Laemmli technique (Laemmli, 1970), by using a 7.5% polyacrylamide gel. This technique allows separating proteins according to their size. After electrophoresis, the protein mixture is electro-transferred onto a nitrocellulose membrane. The membrane is then saturated with non-specific proteins, and then incubated with a 1/10,000 dilution of a polyclonal antibody against RNase E, raised in rabbits. The regions of the membrane having fixed the anti-RNase E antibody are detected, by incubating this latter with a goat antibody raised against rabbit IgG, and coupled to peroxidase enzyme. The presence of the peroxidase on the membrane is itself revealed by the electrochemiluminescence (ECL) technique, using a kit sold by Amersham. This technique permits determining to what position has migrated the RNase E polypeptide synthesized by each of the candidates, and thus the size of this polypeptide. In particular, the reduction in size occasioned by the G2196T mutation is immediately visible in these tests. More than half of the thermoresistant candidates obtained in this experiment possess the desired mutation.

Particular case of the rne131 mutation.

The protocol described above was also used to introduce onto the BL21(DE3) chromosome spontaneous mutations (such as rne131) isolated by Kido et al., and also leading to the synthesis of a truncated RNase E. However, these mutations being from the outset localized on the chromosome, the protocol thereof was simplified.

The BZ31 strain (Kido et al., 1996) carries the rne131 mutation. By virtue of the transduction by P1 bacteriophage (Silhavy et al., 1984; see above), there is transposed in BL21(DE3)rne1 the region of the BZ31 chromosome surrounding the rne locus by selecting transductance capable of growing at 42° C. Next, it is verified that these clones sufficiently synthesize a truncated RNase E polypeptide by using the "Western" technique described above. All of the tested candidates (6/6, or 100%) acquired the desired modification. Incidentally, it was also observed, as was expected in view of the experiment for constructing BL21(DE3)rne1, that 50% of the thermoresistant transductants also acquired the wild-type zce-726 locus, and therefore once again became sensitive to tetracycline (Tet$^S$). In the following, a Tet$^S$ candidate called BL21(DE3)rne131 was chosen.

3) Utilization of the BL21(DE3)rneG2196T or BL21 (DE3) rne131 strains for efficient gene expression, controlled by the T7 promoter Principle. The rneG2196T or rne131 mutations cause overall stabilization of m-RNA by a factor of about 2. However, this stabilization is not uniform for all of the m-RNAs. In particular, no doubt because of the particular properties of T7 RNA polymerase (which enzyme has an elongation speed much higher than that of the ribosomes which translate the message; see above), the m-RNA synthesized by this enzyme seems as advantageously stabilized as the majority of cellular m-RNA. It therefore results that the proportion of the total proteins constituted by the products of these particular m-RNAs, is increased when a mutation such as rneG2196T or rne131 is present in the cell. This observation is the basis of the present invention. Several examples are given below.

Quantitative evaluation of the invention: the lacZ gene as a model system. Several years ago, the inventors described the construction of a BL21(DE3) derivative, called ENS134, which comprises a copy of the lacZ gene inserted in the malA region of the chromosome (Iost & Dreyfus, 1995; Lopez et al., 1994). This gene, which codes for an E. coli enzyme—β-galactosidase—whose expression is especially easy to quantify (Miller, 1972), is placed under the control of the T7 promoter. It is followed by a gene coding for a particular t-RNA, t-RNA$^{Arg5}$ of E. coli, whose expression provides a convenient measure of the level of transcription (Lopez et al., 1994). This well-defined system permits particularly reproducible measurements of the stability of a particular m-RNA synthesized by T7 polymerase, as well as of the yield of the corresponding polypeptide. By that test, the rne131 mutation was introduced in ENS134 as described above for BL21(DE3). We grew ENS134 cells, or the derivative thereof carrying the mutation, at 37° C. As regards the culture medium, we used a rich synthetic medium or a minimum medium (Neidhart et al., 1974), in the presence of IPTG (isopropyl β-D-thiogalactopyranoside; this is an inductor whose presence is necessary for the synthesis of T7 polymerase in BL21(DE3); Studier & Moffat, 1986). The cells are harvested in exponential phase, then lysed by sonication, whereupon β-galactosidase is determined in the cellular; extract, either by measuring enzymatic activity, or by examining the abundance of the β-galactosidase polypeptide by electrophoresis according to Laemmli. It is observed that the presence of the mutation enhances the expression of β-galactosidase by a factor of about 25 in rich medium, or 80 in acetate minimum medium, without affecting the level of transcription of the gene. This result, obtained with a model system, illustrates the possibilities of the invention.

Expression of cloned eukaryotic genes in E. coli. In expression systems based on the properties of T7 polymerase, the gene to be expressed—generally a eukaryotic gene—is fused downstream of the T7 promoter and a ribosome fixation site (RBS) permitting the translation in E. coli. The construct is inserted into a multicopy plasmid derived from pBR322, designated pET, and placed in the BL21(DE3) strain or in one of its derivatives (Dubendorff & Studier, 1991; Studier & Moffat, 1986; Studier et al., 1990.) As above, expression of the gene to be expressed—the "target" gene—is initiated by addition of the IPTG inducer to the culture medium, which causes synthesis of T7 polymerase. However, in contrast to the model system described above, the induction by IPTG in this case may be only transitory, as the transcription of the gene from the T7 promoter is so active, that it kills the cells when this promoter is present on a multicopied plasmid.

There were introduced into BL21(DE3), and into BL21 (DE3)rne131 or BL21(DE3)rneG2196T, pET plasmids comprising a certain number of eukaryotic genes, namely the Krox-20 gene implicated in the precocious development of mice (Vesque & Charnay, 1992), the engrailed-2 gene implicated in the morphogenesis of chicken embryo (Logan et al., 1992), and the gene coding for HTLV1 protease, a human retrovirus (Malik et al., 1988). The cells are caused to grow to a DO$_{600}$ of about 0.5, then IPTG is added. The cells were harvested four hours later. There was thus obtained a cellular extract that is analyzed by electrophoresis as described above. In the three cases, detection of the product of the "target" gene is performed by the "Western" technique (polyclonal and monoclonal antibodies raised against Krox-20 and engrailed-2, respectively, have been described: (Patel et al., 1989; Vesque and Charnay, 1992)). It could be observed that the product of the "target" gene is three to ten times more abundant when the host is BL21(DE3)rne131 rather than BL21(DE3).

REFERENCES

Babitzke, P. & Kushner, S. R. (1991). The ams (altered mRNA stability) protein and ribonuclease E are encoded by the same structural gene of Escherichia coli. Proc. Natl. Acad. Sci. USA 88, 1–5.

Bradford, M. M. (1976). A rapid and sensitive method for the quantification of microgram quantities of proteins utilizing the principle of protein-dye binding. Anal. Biochem. 72, 248–254.

Carpousis, A. J., Van Houwe, G., Ehretsmann, C. & Krisch, H. M. (1994). Copurification of E.coli RNAase E and PNPase: Evidence for a specific association between two enzymes important in RNA processing and degradation. Cell 76, 889–900.

Casaregola S., Jacq A., Laoudj D., McGurk G., Margarson S., Tempete M., Novis V. et Holland I. B. (1992). Cloning and analysis of the entire E. coli ams gene. ams is identical to hmpi and encodes a 114 kDa protein that migrates as a 180 kDa protein. *J. Mol. Biol.* 228, 30–40. Erratum (1994) *J. Mol. Biol.* 238, 867.

Christie, G. E., Farnham, P. J. & Platt, T. (1981). Synthetic sites for transcription termination and a functional comparison with tryptophan operon termination sites in vitro. *Proc. Natl. Acad. Sci. USA* 78, 4180–4184.

Cohen, S. N. & Mc Dowall, K. J. (1997). RNase E: still a wonderfully mysterious enzyme. *Mol. Microbiol.* 23, 1099–1106.

Dente, L., Cesareni, G. & Cortese (1983). pEMBL: a new family of single-stranded plasmids. *Nucl. Acids Res.* 11, 1645–1655.

Dreyfus, M. (1988). What constitutes the signal for the initiation of protein synthesis on *Escherichia coli* mRNAs? *J. Mol. Biol.* 204, 79–94.

Dubendorff, J. W. & Studier, W. F. (1991). Controlling basal expression in an inductible T7 expression system by blocking the target T7 promotor with lac repressor. *J. Mol. Biol.* 219, 45–59.

Iost, I. & Dreyfus, M. (1994). mRNAs can be stabilized by DEAD-box proteins. Nature. 372, 193–196.

Iost, I. & Dreyfus, M. (1995). The stability of the *E. coli* lacZ mRNA depends upon the simultaneity of its synthesis and translation. *EMBO J.* 14, 3252–3261.

Kido M., Yamanaka K., Mitani T., Niki H., Ogura T. and Hiraga S. (1996). RNase E polypeptides lacking a carboxyl-terminal half suppress a mukb mutation in *Escherichia coli*. J. Bacteriol., 178, 3917–3925.

Kunkel, T. A., Roberts, J. D. & Zakour, R. A. (1987). Rapid and efficient site-specific mutagenesis without phenotypic selection. In *Methods in Enzymology*, pp. 367–382.

Laemmli, U. K. (1970). Cleavage of structural proteins during assembly of the head of bacteriophage T4. *Nature* 227, 680–685.

Logan, C., Hanks, M., Noble-Topham, S., Nallainathan, D., Provart, N. J. & Joyner, A. L. (1992). Cloning and sequence comparison of the mouse, human and chicken engrailed genes reveal potential functional domains and regulatory regions. *Dev. Genet.* 13, 345–358.

Lopez, P. J., Iost, I. & Dreyfus, M. (1994). The use of a tRNA as an transcriptional reporter: the T7 late promoter is extremely efficient in *Escherichia coli* but its transcripts are poorly expressed. *Nucl. Acids Res.* 22, 1186–1193. Erratum 22, 2434.

Lopez, P. J., Marchand I., Joyce S. A and Dreyfus, M. (1999). The C-terminal half of RNase E, which organizes the *Escherichia coli* degradosome, participates in mRNA degradation but not in RNA processing in vivo, *Mol.Microbiol* 33, 188–1999.

McDowall, K. J., Hernandez, R. G., Lin-Chao, S. and S. N., Cohen. (1993). The ams-1 and rne-3071 temperature-sensitive mutations in the ams gene are close proximity to each other and cause substitutions within a domain that resembles a product of the *Eschericia coli* mre locus. *J. Bacteriol.* 175, 4245–4249.

Makarova, O. V., Makarov, E. M., Sousa, R. & Dreyfus, M. (1995). Transcribing *Escherichia coli* genes with mutant T7 RNA polymerases: stability of lacz mRNA inversely correlates with polymerase speed. *Proc. Natl. Acad. Sci. USA* 92, 12250–12254.

Malik, K. T., Even, J., et Karpus A. (1988). Molecular cloning and complete nucleotide sequence of an adult T cell leukaemia virus type I (ATLV/HTLV-1) isolate of Carribean origin: relationship to other members of the ATLV/HTLV-1 subgroup. *J. Gen. Virol.* 69, 1695–1710.

Miczak, A., Kaberdin, V. R., Wei, C. L. & Lin-Chao, S. (1996). Proteins associated with RNase E in a multicomponent ribonucleolytic complex. *Proc. Natl. Acad. Sci. USA* 93, 3865–3869.

Miller, J. H. (1972). *Eperiments in Molecular Biology*, Cold Spring Harbor Laboratory Press, Cold Spring Harbor, N.Y.

Mudd, E. A., Carpousis, A. J. & Krisch, H. M. (1990a). *E. coli* RNase E has a role in the decay of bacteriophase T4 mRNA. *Genes and Development* 4, 873–881.

Mudd, E. A., Krisch, H. M. & Higgins, C. F. (1990b). RNase E, an endoribonuclease, has a general role in the chemical decay of *Escherichia coli* mRNA: evidence that rne and ams are the same genetic locus. *Mol. Microbiol.* 4, 2127–2135.

Neidhart, F. C., Bloch, P. L. & Smith, D. F. (1974). Culture medium for Enterobacteria. *J. Bacteriol.* 119, 736–747.

Ono, M. & Kuwano, M. (1979). A conditional lethal mutation in an *E. coli* strain with a longer chemical lifetime of messenger RNA. *J. Mol. Biol.* 129, 343–357.

Patel, N. H., Martin, B. E., Coleman, K. G., Poole, S. J., Ellis, M. C., Kornberg, T. B. & Goodman, C. S. (1989). Expression of engrailed proteins in arthropods, annelids, and chordates. *Cell* 58, 955–968.

Py, B., Higgins, C. F., Krish, H. M. & Carpousis, A. J. (1996). A DEAD-box RNA helicase in the *Escherichia coli* RNA degradosome. *Nature* 381, 169–172.

Sambrook, J., Fritsch, E. F. & Maniatis, T. (1989). *Molecular cloning: a laboratory manual*. (Sambrook, J., Fritsch, E. F. & Maniatis, T., Eds.), Cold Spring Harbor Press, Cold Spring Harbor.

Silhavy, T. J., Berman, M. L. & Enquist, L. W. (1984). *Experiments with gene fusions*, Cold Spring Harbor Laboratory, Cold Spring Harbor.

Studier, F. W. & Moffat, B. A. (1986). Use of bacteriophage T7 RNA polymerase to direct selective high-level expression of cloned genes. *J. Mol. Biol.* 189, 113–130.

Studier, F. W., Rosenberg, A. H., Dunn, J. J. & Dubendorff, J. W. (1990). Use of T7 RNA polymerase to direct expression of cloned genes. In *Methods in Enzymology* (Academic Press, ed.), Vol. 185, pp. 60–89.

Tabor, S. & Richardson, C.C. (1985). A bacteriophage T7 RNA polymerase/promoter system for controlled exclusive expression of specific genes. *Proc. Natl. Acad. Sc. USA* 82, 1074–1078.

Vesque, C. & Charnay, P. (1992). Mapping functional regions of the segment-specific transcription factor Krox-20. *Nucl. Acids. Res.* 20, 2485–2492.

What is claimed is:

1. A process for producing predetermined recombinant polypeptides or proteins, comprising expressing said polypeptides or proteins in *Escherichia coli* (*E. coli*) strains whose gene encoding RNase E comprises a mutation such that the enzyme produced upon expression of this mutated gene no longer possesses activity for degrading messenger RNA (m-RNA), said mutation not significantly affecting growth of the said *E. coli* strains, and wherein said mutation corresponds to the substitution of the guanine G at position 2196 of SEQ ID NO:1, by a thymidine T, so as to create a stop codon TAA situated at the positions 2196 to 2198 of SEQ ID NO: 1.

2. The process according to claim 1, characterized in that the gene encoding RNase E comprises a mutation such that the enzyme produced upon expression of this mutated gene preserves the activity for maturation of ribosomal RNA (r-RNA) of the RNase E, but no longer possesses activity for degradation of m-RNA.

3. The process according to claim 1, characterized in that the mutation causes the deletion of 476 amino acids of the sequence of RNase E represented by SEQ ID NO: 2.

4. The process according to claim 1, characterized in that the said strains contain an exogenous inducible expression system, under the control of which is placed the expression of the predetermined recombinant polypeptides, and wherein the expression system compromises RNA polymerase of the T7 bacteriophage.

5. *E. coli* strains transformed such that they contain an inducible expression system, and whose gene encoding RNase E comprises a mutation such that the enzyme produced upon expression of this mutated gene no longer possesses activity for degradation of m-RNA, this mutation not significantly affecting growth of the said *E. coli* strains, and wherein said mutation corresponds to the substitution of the guanine G at position 2196 of SEQ ID NO:1, by a thymidine T, so as to create a stop codon TAA situated at the positions 2196 to 2198 of SEQ ID NO: 1.

6. *E. coli* strains according to claim 5, transformed such that they contain an exogenous inducible expression system, and whose gene encoding RNase E comprises a mutation such that the enzyme produced upon expression of this mutated gene conserves the activity for maturation of r-RNA of the RNase E, but no longer possesses activity for degradation of m-RNA.

7. *E. coli* strains according to claim 5, characterized in that the inducible expression system uses RNA polymerase of the T7 bacteriophage.

8. *E. coli* strains according to claim 5, characterized in that the mutation causes the deletion of 476 amino acids of the sequence of RNase E represented by SEQ ID NO:2.

9. *E. coli* strains according to claim 5, characterized in that the inducible expression system controls the transcription of a DNA sequence encoding one or several predetermined recombinant polypeptides.

10. A process for producing predetermined recombinant polypeptides, characterized in that it comprises:

transforming *E. coli* strains with a plasmid vector containing a nucleotide sequence encoding one or several recombinant polypeptides, wherein said *E. coli* strains are transformed such that they contain an inducible expression system, and whose gene encoding RNase E comprises a mutation such that the enzyme produced upon expression of this mutated gene no longer possesses activity for degradation of m-RNA, said mutation not significantly affecting growth of said *E. coli* strains, said mutation corresponds to the substitution of the guanine G at position 2196 of SEQ ID NO:1, by a thymidine T, so as to create a stop codon TAA situated at the positions 2196 to 2198 of SEQ ID NO: 1, culturing the transformed *E. coli* strains obtained in the preceding step, for a time sufficient to permit expression of the recombinant polypeptide or polypeptides in the *E. coli* cells, and recovery of the recombinant polypeptide or polypeptides produced during the preceding step.

11. Process for producing predetermined recombinant polypeptides according to claim 10, characterized in that it comprises:

a step of transforming *E. coli* strains, with a plasmid vector containing the nucleotide sequence encoding one or several recombinant polypeptides, so as to obtain *E. coli* strains, in which transcription of the said nucleotide sequence encoding one or several recombinant polypeptides is placed under control of an inducible expression system, culturing the transformed *E. coli* strains obtained during the preceding step, and inducing the said expression system, for a time sufficient to permit expression of the recombinant polypeptide or polypeptides in the *E. coli* cells, and recovery of the recombinant polypeptide or polypeptides produced during the preceding step.

* * * * *